United States Patent
Chan et al.

(10) Patent No.: US 6,852,527 B2
(45) Date of Patent: Feb. 8, 2005

(54) APPARATUS AND METHOD FOR THE MEASUREMENT OF CELLS IN BIOLOGICAL SAMPLES

(75) Inventors: Anthony Chan, Cupertino, CA (US); Richard M. Rocco, Los Altos, CA (US)

(73) Assignee: Inovyx, Inc., Mountain View, CA (US)

(*) Notice: Subject to any disclaimer, the term of this patent is extended or adjusted under 35 U.S.C. 154(b) by 249 days.

(21) Appl. No.: 10/165,742

(22) Filed: Jun. 6, 2002

(65) Prior Publication Data

US 2003/0228705 A1 Dec. 11, 2003

(51) Int. Cl.[7] .............................................. C12M 1/34
(52) U.S. Cl. ................... 435/288.7; 435/4; 435/308.1; 356/246; 210/767; 210/85; 210/436; 210/446; 210/496
(58) Field of Search .................. 435/4, 288.7, 308.1; 356/244, 246; 210/767, 85, 435, 436, 445, 446, 496, 505, 506, 508, 509

(56) References Cited

U.S. PATENT DOCUMENTS

| | | | | |
|---|---|---|---|---|
| 3,515,490 A | * | 6/1970 | Dreyfus et al. ............ 356/244 |
| 4,729,949 A | * | 3/1988 | Weinreb et al. ............ 435/30 |
| 4,787,988 A | * | 11/1988 | Bertoncini et al. ........ 210/808 |
| 4,849,061 A | * | 7/1989 | Relyea ...................... 156/308.4 |
| 5,139,685 A | * | 8/1992 | de Castro et al. ......... 210/767 |
| 5,240,861 A | | 8/1993 | Bieri .......................... 436/178 |
| 5,252,293 A | | 10/1993 | Drbal et al. ................ 422/101 |
| 5,266,209 A | * | 11/1993 | Knight et al. .............. 210/691 |
| 5,308,483 A | | 5/1994 | Sklar et al. ................. 210/232 |
| 5,484,572 A | | 1/1996 | Katakura et al. .......... 422/101 |
| 5,733,507 A | | 3/1998 | Zakim ........................ 422/101 |

OTHER PUBLICATIONS

Website print out, "Cyto–Tek MonoPrep System" Sakura Finetek USA inc., 1 page.*
Brochure, StatSpin, an ARIS Company, Cytofuge, "Filter oncentrator Method", 2 pages.*

* cited by examiner

Primary Examiner—David A. Redding
(74) Attorney, Agent, or Firm—Thomas Schneck; David M. Schneck

(57) ABSTRACT

An apparatus and method for concentrating and measuring low levels of cells in biological samples. The apparatus, or concentration device, consists of two chambers with an optically level collection membrane intermediating between the chambers. The collection membrane filters the biological sample, trapping cellular elements of interest. A vacuum may be attached to the device to assist in filtration. The surface area of the collection membrane matches the view field of a standard imaging system and the device can be mounted on a standard microscope stage. All the cells in the sample volume are collected onto the membrane. The view field provides a fixed volumetric area for cell counting. Since the volume of sample tested is known, the total number of cells in the original sample may be calculated. The sample reservoir of the concentration device may also be used for sample preparation. The concentration device is fully-contained; therefore, the investigator does not have to handle the sample once it is placed in the sample reservoir.

38 Claims, 9 Drawing Sheets

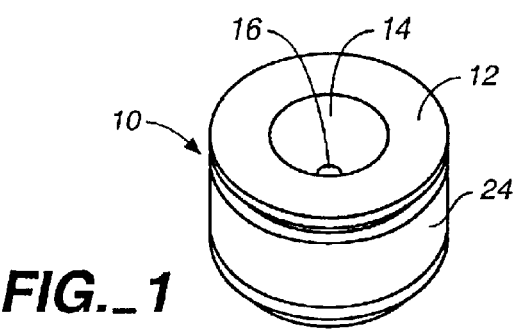
FIG._1
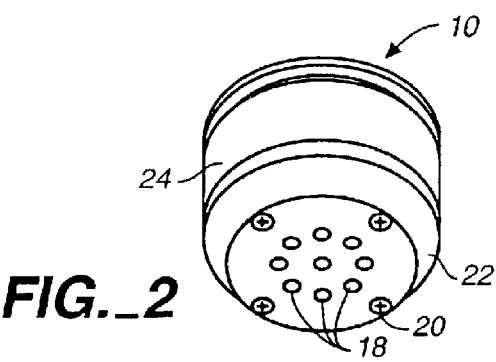
FIG._2
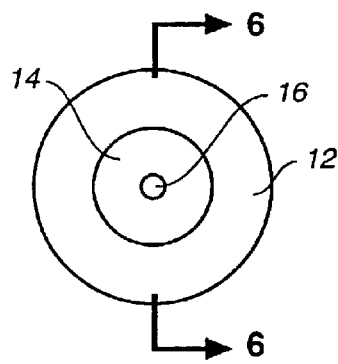
FIG._3
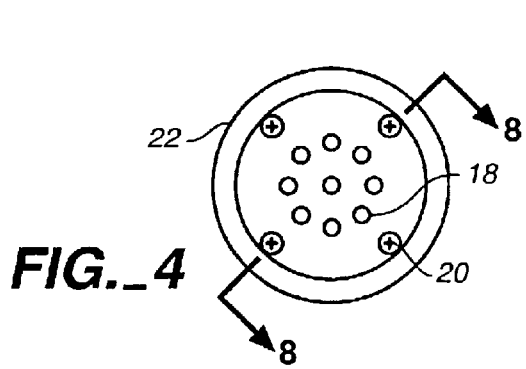
FIG._4
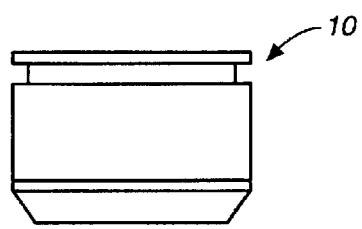
FIG._5A
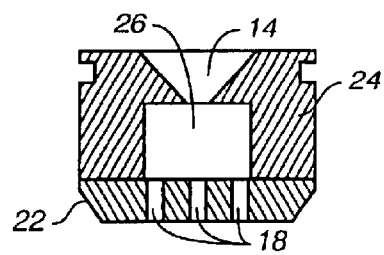
FIG._6
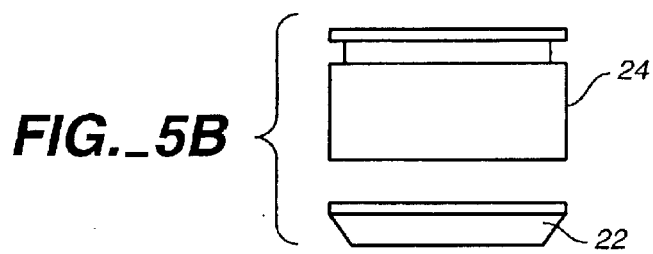
FIG._5B

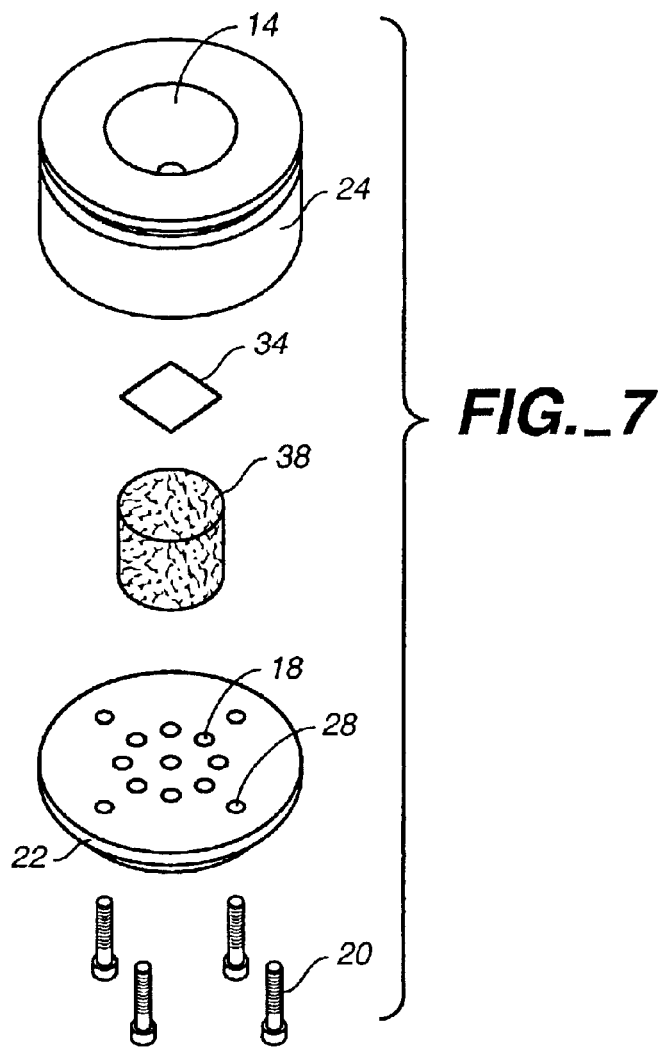
FIG._7
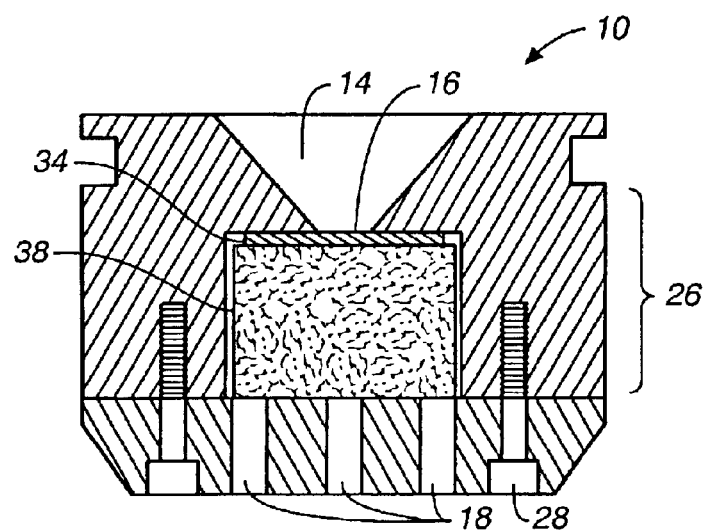
FIG._8

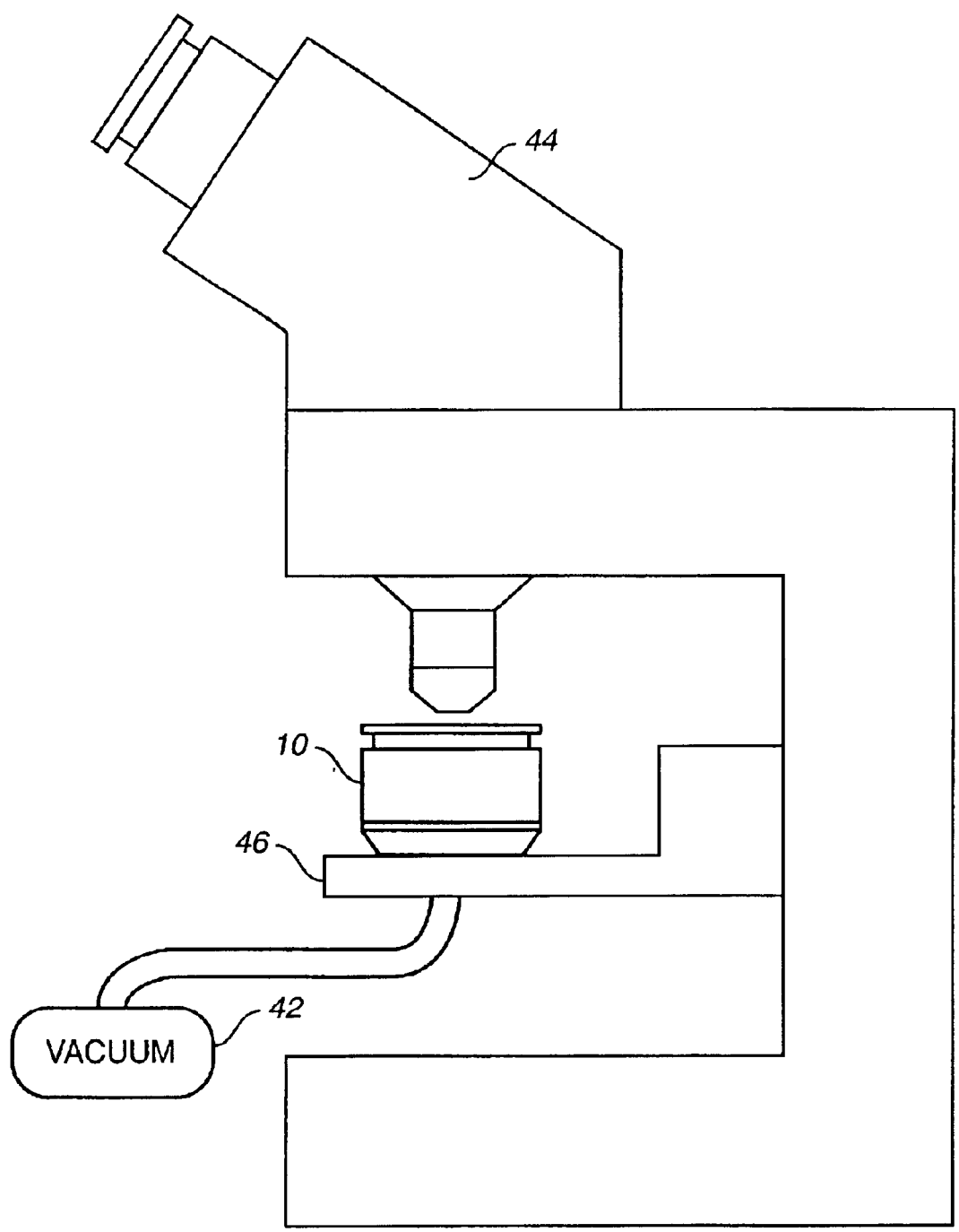
FIG._9

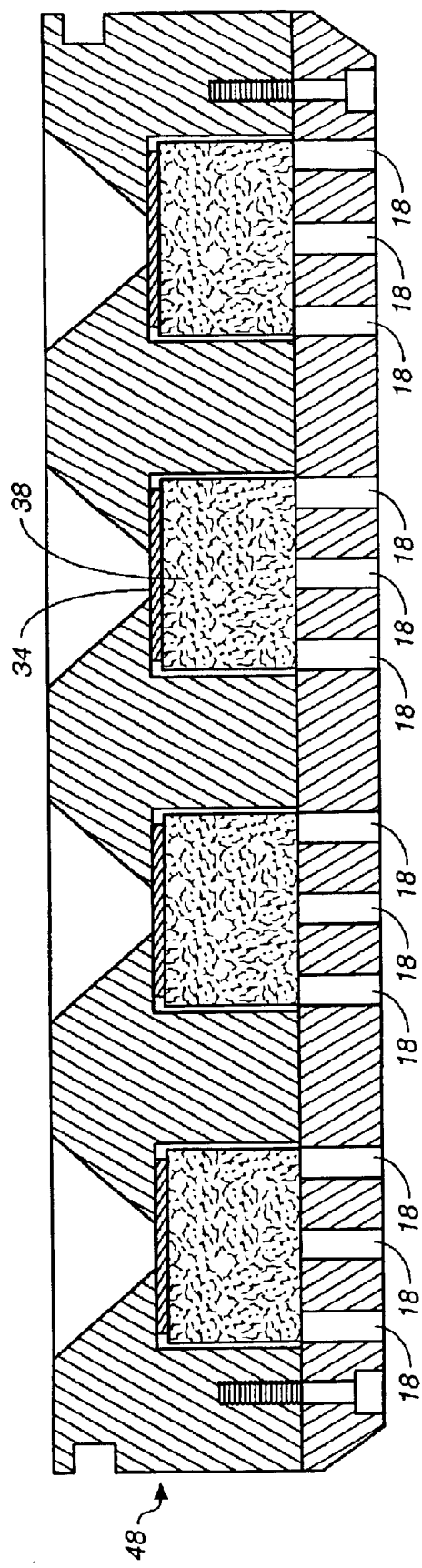
FIG._10

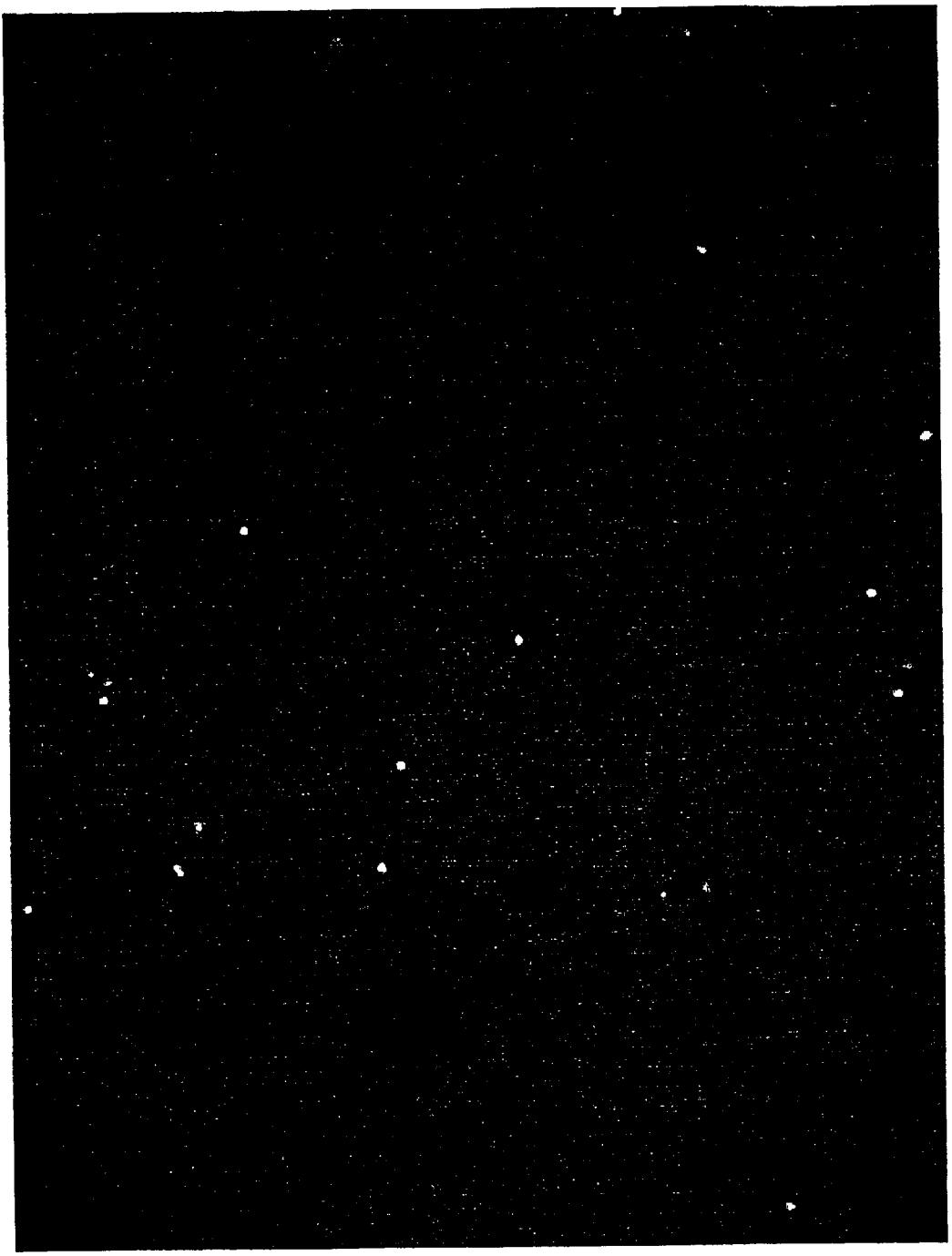
FIG._11

FIG._12

FIG._13

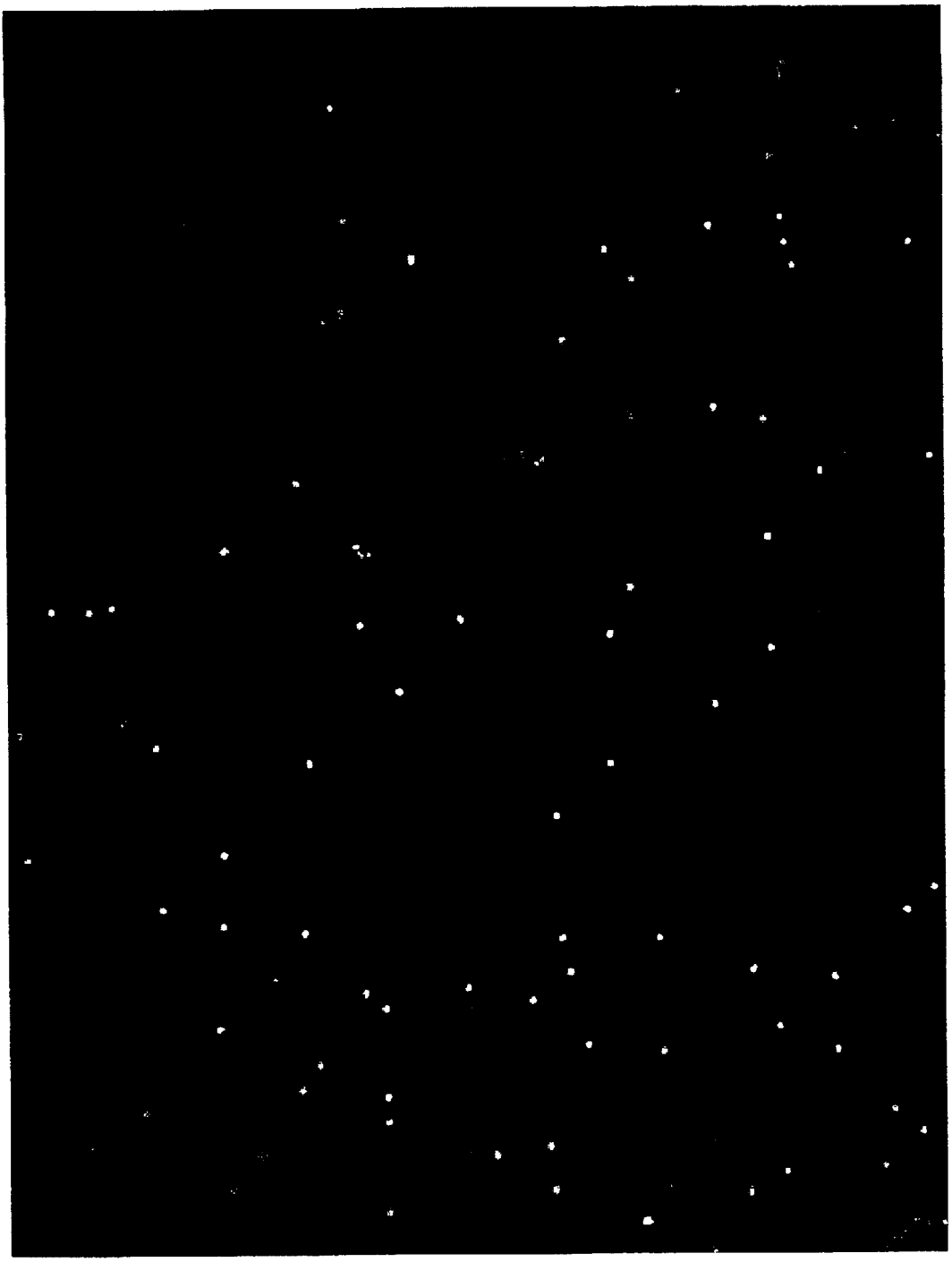
FIG._14

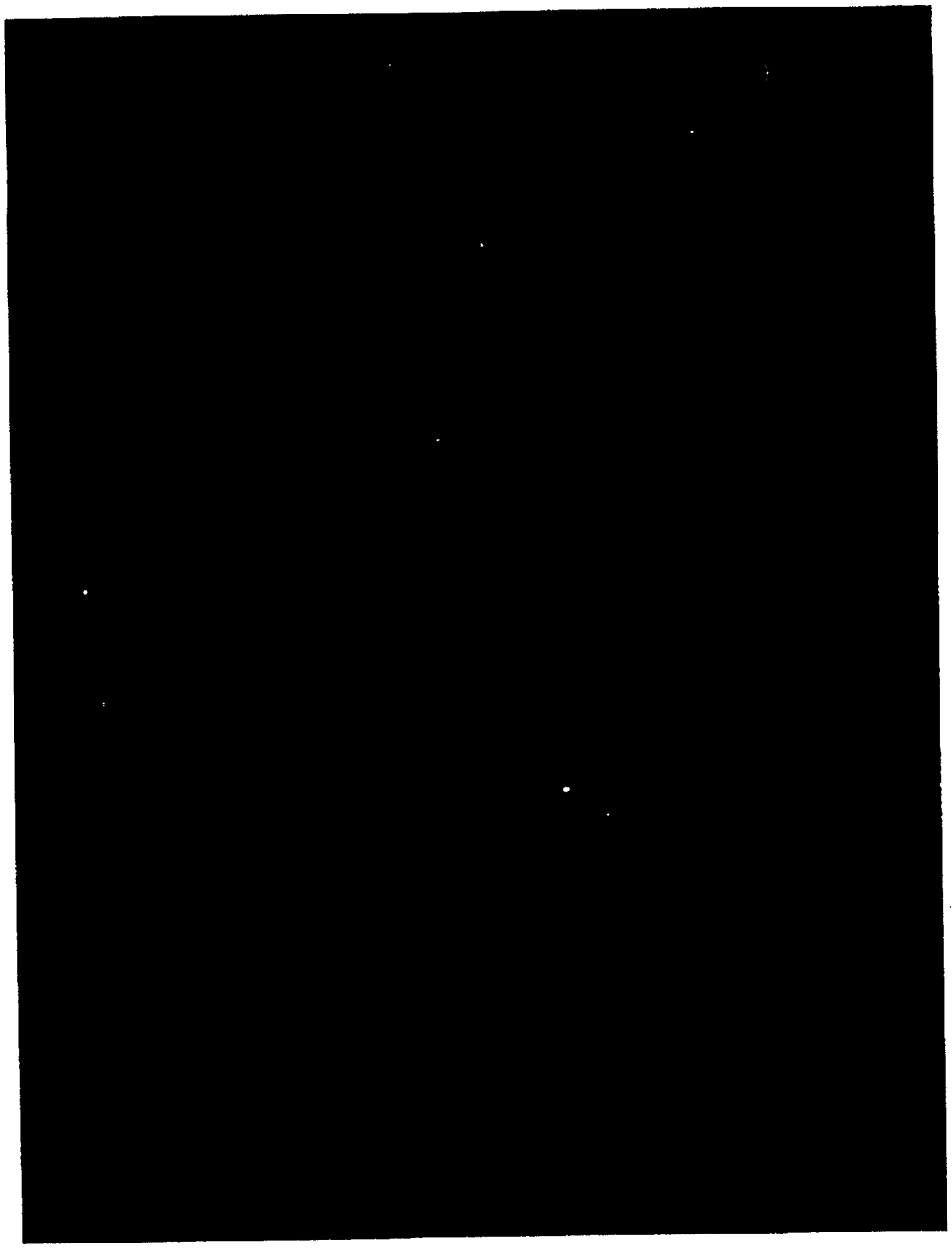
FIG._15

APPARATUS AND METHOD FOR THE MEASUREMENT OF CELLS IN BIOLOGICAL SAMPLES

FIELD OF THE INVENTION

This invention relates to the collection and subsequent measurement of low numbers of cells in biological samples.

BACKGROUND OF THE INVENTION

Accurate and rapid counting of cellular elements in biological fluids is a necessity in the biomedical, pharmaceutical, and biological research fields. While there are many automated and semi-automated instruments for counting and examining cells, these instruments cannot measure low levels of cells (i.e., 100 cells/$\mu$L or less) or require pre-concentration or other time consuming steps to reach this detection level. Various biological fluids have a concentration of cells below 100 cells/$\mu$L and numerous procedures and protocols require that the low levels of cells in these fluids be measured. For instance, the current legal standards for transfusion products allow less than 20 white cells/$\mu$L in the United States and less than 4 white cells/$\mu$L in Europe before the products can be administered to humans. The concentration of both white cells and red cells in cerebrospinal fluid is less than 10 cells/$\mu$L. White and red cell counts are also performed when pleural, abdominal, and pericardial fluids are examined; generally, these cell levels are less than 50 cells/$\mu$L. Stem cell harvesting from donors cannot begin until there is a concentration of at least 10 cell/$\mu$L in the donor's peripheral blood. The presence of rare cells in various biological fluids may indicate cancer or other disease states. Generally these rare cells levels are 0.01 cells/$\mu$L or less. In addition to the difficulty in detecting low concentrations of cells, small sample size also presents a detection challenge. If only a few $\mu$L are available for assay, accurate enumeration of cells is difficult for many analytical systems. An apparatus and method to accurately measure the number of cells in biological fluids with a low or very low cell concentration or with low volumes would be beneficial.

While cell or particle counters are available, they do not accurately detect low levels of cells. For instance, presently commercially available automated cell or particle counters cannot measure cells levels below 500 to 1000 cells/$\mu$L. At a concentration of 10 cells/$\mu$L, the bias between manual and automated cell counting procedures has been reported be 999%. (Rabinovitch, A. and Cornbleet, P. J., Arch Pathol Lab Med, 118:13–17, 1994) In addition, fluidic elements used by these cell detection systems may be clogged up by viscous body fluids.

Flow cytometry methods may be employed to detect a low concentration of cells. However, large sample volumes are generally required in order for this process to be accurate. Flow cytometry systems achieve acceptable accuracy levels when 10,000 or more cells are counted; the error rate in samples having a concentration of 8 cells/$\mu$L has been reported to be 45%. (Dumont, L. J. and Dumont, D. F., Cytometry, 26:311–316, 1996) In a spinal fluid sample which contains 5 white cells/$\mu$L, a sample of 2 mL would be required in order for the system to detect 10,000 cells. A repeat second assay would also require 2 mL. In both pediatric and adult patients, the total volume of spinal fluid removed rarely exceeds 4 mL. Therefore, if flow cytometry were used to quantify the number of cells in a sample, all the fluid removed from the patient would have to be used for flow cytometry measurements; none would be available for the many other chemistry, microbiology, and cytology assays which are essential to spinal fluid procedures. Flow cytometers also encounter difficulty when viscous samples, such as body fluids, are analyzed because the samples may clog up the fluidics of the flow cytometer. Given these problems, flow cytometry may not be a practical solution to detecting low concentrations of cells.

A manual counting technique, employing a hemacytometer with either light or fluorescent microscopy may be used to count cells present in low concentrations. When a fixed-volume hemacytometer is used, a sample of biological fluid is diluted with a buffer-stain solution which keeps the cells intact and stains the cells so they are detectable. Either light or fluorescent microscopy is used (depending on the cell stain) to count the cells after a sample is loaded into the hemacytometer. A dilution calculation is used to determine the total number of cells per $\mu$L in the sample. This process is labor-intensive, time-consuming, and subject to human error.

Another drawback to using a hemacytometer is a lack of accuracy. The standard sample volume is 0.5 $\mu$L. Samples are usually diluted by a factor of two or more. Assuming a dilution factor of two, a sample with 10 cells/$\mu$L will have 5 cells/$\mu$L after dilution. If the sample volume is 0.5 $\mu$L, only 2.5 cells will be present in the hemacytometer. Given these low levels of cells, it is difficult to achieve accurate measurements.

The Nageotte hemacytometer overcomes some of the limitations of standard hemacytometers. The Nageotte hemacytometer has a sample volume of 50 $\mu$L and is used to measure the levels of white cells in transfusion products. A dilution factor of 10 using staining reagent is required in order to reduce background debris in the sample and make cell counting easier. As noted above, European regulations prohibit administration of a transfusion product that contains more than 4 white cells/$\mu$L. Given this limit, a liquid containing 4 cells/$\mu$L contains 0.4 cells/$\mu$L once it is diluted by a factor of ten. Since a 50 $\mu$L sample is examined in the Nageotte hemacytometer, 20 cells should be counted. However, studies indicate there is a 40% error rate for this procedure. (Rebulla, P. and Dzik, W., Vox Sang, 66:25–32, 1994).

A number of concentration procedures have been introduced to reduce the imprecision of low level cell counting methods by concentrating the cell levels prior to analysis. In one approach, 10 mL of a transfusion product is diluted with staining reagent. The diluted sample is centrifuged at 1000 g for 15 minutes. A second centrifugation at 300 g pellets the cells, allowing decanting of the supernatant. Cells in the concentrated sample volume are counted by manual and automated techniques. At cell counts below 1 cell/$\mu$L although the error rate was reported to range up to 36.2%. (Szuflad, P. and Daik, W. H., Transfusion, 37:277–283, 1997).

Various commercial procedures, designed to concentrate low levels of various biological fluids onto a slide for staining and subsequent cytopathology examination, are available. The CYTOFUGE™ 2 system from StatSpin, Inc. uses a disposable plastic cup fitted tightly against a standard glass slide. The sample to be concentrated is introduced into the cup and the device is then centrifuged. Cells are forced through the fluid onto the controlled small surface of the glass slide. The slide is then removed, stained, and examined. Similar systems are available from Wescor and Thermo Shandon.

The MonoPrep 2 system from MonoGen, Inc. uses a syringe assembly to concentrate cells onto a membrane. A plastic housing is attached to a standard 10 mL plastic syringe. The sample to be concentrated is aspirated into the syringe through the membrane. The cells are trapped onto the membrane as the liquid is drawn into the syringe. The membrane is then removed from the syringe housing and the cells transferred to a glass slide for cytopathology examination.

The prior art contains several other solutions to problems with filtration and concentration of samples. For instance, U.S. Pat. No. 5,252,293 discloses a slide with a porous membrane which can filter a sample at various locations on the slide. The slide and membrane provide a filter device with a capture surface for binding agents such as antibodies. The membrane is removed from a concentration device prior to analysis.

U.S. Pat. No. 5,308,483 discloses an in-line filter assembly where the filter membrane can be removed for identification or analysis of the material filtered from the fluid sample. U.S. Pat. No. 5,733,507 discloses a biological cell sample holder for use in infrared and/or Raman spectroscopy. A sample is added to the window of a sample holder, which selectively retains cells while the other components are filtered through the window. U.S. Pat. No. 5,484,572 is a fully-contained apparatus for collecting cells in fluid. A sample fluid is placed in a cup container. The cup container is pressurized and the fluid is forced through an outlet containing a specimen collection film. Specimen cells are captured on the film while the rest of fluid is filtered to another collection container. The specimen film may be removed for further analysis.

U.S. Pat. No. 5,240,861 discloses a device for concentrating liquid specimens which consists of a receptacle containing a membrane. The sample to be concentrated is placed in the receptacle on the upper surface of the membrane. A piston is screwed down toward the upper surface of the membrane, increasing pressure above the membrane and forcing small particles through the membrane. The sample is concentrated, for example, by having water removed from it. After the desired level of concentration is reached, the filtrate may be removed from the receptacle for further analysis.

None of the prior art discussed here discloses an apparatus that can concentrate a liquid specimen and subsequently allow automated cell enumeration in a single viewing.

None of the prior art discussed here shows a self-contained apparatus which prepares a sample for quantitative cell counting.

None of the prior art discussed above discloses a method to prepare a sample containing low levels of cellular elements for quantitative cell counting by standard imaging equipment.

SUMMARY OF THE INVENTION

The objects are achieved by an apparatus and method for preparing, concentrating, and analyzing a biological specimen. The apparatus provides a uniform, optically-level surface for a collection membrane which filters the biological sample, trapping cellular elements of interest. In one embodiment, the collection membrane is a polycarbonate track-etched membrane. The membrane has uniform pores sized to ensure cellular elements of interest are trapped on the membrane surface.

The apparatus can be placed directly onto a standard microscope stage for image analysis. The collection membrane has a view field, chosen to match the field of view of the imaging system used to count the cells. The view field provides a fixed volumetric area for cell counting and the total number of cells in the sample may be calculated.

The apparatus has two chambers. A collection membrane sits between the two chambers and placed in a optically flat position. The absorbent pad disposed in the second chamber traps liquid from the biological sample. The absorbent pad may absorb several applications of the biological sample which would allow the concentration of cellular elements collected on the membrane. The absorbent pad may be hydrophobic or hydrophilic.

In one embodiment, the top chamber, which receives the biological sample, has side walls that are sloped to provide optimum flow for the sample and are treated to prevent cell adhesion. The top chamber also provides a reservoir where reagents and the sample may be mixed prior to concentration and image analysis.

Cellular elements are trapped on the collection membrane as sample fluid flows through the collection membrane. A vacuum may to be applied in order to force sample flow. This vacuum may be provided by either a small automated pumping system or a syringe attached at a port in the bottom chamber. Generally, only low pressure need be applied in order to concentrate the sample. This approach provides a more rapid analysis than methods employing a centrifuge.

After the sample has been prepared and concentrated, the entire apparatus may be placed on a microscope stage for fluorescent or other microscopic analysis. The collection membrane and the absorbent pad may be white or black, depending on the wavelength of light being used in the optical system used for counting cells.

Since sample preparation, such as labeling, can be conducted within the apparatus, which is fully-contained, the investigator does not have to handle the sample once it is put into the apparatus. This improves the accuracy of the results because the sample is less likely to be contaminated as a result of transfer to different devices. The use of a low-pressure vacuum to concentrate the sample, rather than a centrifuge, prevents the possibility of air-borne aerosol contamination. Since the sample is always contained in the apparatus, the investigator's risk of exposure to the sample is also reduced and can be disposed of safely.

BRIEF DESCRIPTION OF THE DRAWINGS

FIG. 1 is a top perspective view of the concentration device.

FIG. 2 is a bottom perspective view of the device shown in FIG. 1.

FIG. 3 is an overhead view of the device shown in FIG. 1.

FIG. 4 is a bottom view of the device shown in FIG. 1.

FIG. 5a is a side view of the device shown in FIG. 1.

FIG. 5b is a partially exploded view of the device shown in FIG. 1.

FIG. 6 is a cross-section of the device shown in FIG. 3 without the membrane or absorbent pad.

FIG. 7 is an exploded view of the device shown in FIG. 1.

FIG. 8 is a cross-section of the device shown in FIG. 4.

FIG. 9 shows the device mounted on a microscope stage in accordance with the invention.

FIG. 10 shows an embodiment of the cell concentrator in an array on a multi-well plate in accordance with the invention.

FIG. 11 is an image of fluorescently-labeled latex beads trapped on the device's collection membrane.

FIG. 12 is an image of spinal fluid white cells trapped on the device's collection membrane.

FIG. 13 is an image of granulocytes trapped on the device's collection membrane.

FIG. 14 is an image of somatic cells in raw whole milk trapped on the device's collection membrane.

FIG. 15 is an image of apheresis platelets trapped on the device's collection membrane.

DETAILED DESCRIPTION OF THE INVENTION

The concentration device ("device") 10 is shown in FIG. 1. Specimens are placed in cone 14 in the top surface 12 of the device 10. The specimen flows through the opening 16 at the bottom of cone 14; cells of interest are trapped on a membrane at the opening 16, which matches the field of view of the imaging system being used to count the cells trapped on the membrane. The fluid in the specimen, which is not trapped on the membrane, flows into the second chamber of the device 10 (see FIG. 6, below). Both cone 14 and the second chamber are contained in the main body 24 of the device 10.

As shown in FIG. 2, the bottom portion 22 of the device 10 is attached to the main body 24 by screws 20. The bottom portion 22 of the device 10 also features a vacuum port 18 where a vacuum system may be attached.

An overhead view of the device is provided in FIG. 3. A cone 14 which receives specimens is cut into the top surface 12. The walls of cone 14 are smooth and treated to prevent cell adhesion and are sloped (in this embodiment, the slope is 35 degrees) to provide optimal flow of the sample and clear of the optical path of the measurement device. Among the treatments for the walls of the cylinder 14 are TEFLON™ silicone, wetting agents of various types and proteins such as bovine serum albumin or polyvinyl alcohol (PVA) or polyvinyl-pyrro-lidone (PVP).

The bottom 22 of the device is shown in FIG. 4. The bottom section 22 of the device is fastened to the rest of the device by screws 20. A vacuum port 18 is also provided having 9 holes. Vacuum pressure from a pressure source is used to force sample flow through the collection membrane as suction is applied through ports 18.

The device 10 is shown in profile in FIG. 5a. The main body 24 and the bottom portion 22 of the device are illustrated in FIG. 5b. In this embodiment, the main body 24 and the bottom portion 22 of the device are constructed of DELRIN™ (in other embodiments, other material may be used).

With respect to FIG. 6, a cross-section of the device shows two chambers. The first is cone 14 where the sample is placed. The second chamber 26 is immediately below the first chamber and receives the sample fluid that flows through the collection membrane (the contents of the second chamber 26 will be discussed below in FIGS. 7 and 8). The first and second chambers 14, 26 are contained in the main body 24 of the device. The vacuum ports 18 are located in the bottom portion 22 of the device 22, such that the vacuum is affixed directly below the second chamber 26.

An exploded view of this embodiment of the device is presented in FIG. 7. The device consists of: a main body 24 containing a cylinder 14; a collection membrane 34 which trap cells or particles of interest; an absorbent pad 38 (which in this embodiment is constructed of sintered, porous plastic); and the bottom portion 22 of the device, containing a vacuum port 18 and holes 28 for screws 20, which fasten together the bottom 22 and main body 24 of the device.

The collection membranes 34 are made of solid polycarbonate and typically are $10\mu$ thick. These membranes are commercially available from suppliers including Whatman, Osmonics, Millipore, and SPI. The membranes 34 have uniform pores (e.g. etched holes) ranging from 0.1 to $20\mu$ in diameter, depending on the application. Holes smaller than $1\mu$ are generally used since most cellular elements of interest, such as platelets, white cells, and red cells, range from 2 to $20\mu$ in size; using holes smaller than $1\mu$ ensures that elements of interest are trapped on the membrane. As used herein, cells and cellular elements refers to live or dead cells, discrete cell fragments, beads or particles or other discrete, particulate targets the size of biological cells.

A number of constraints control the hole size and open area (hole count) selection of the membrane for a given test: the largest size hole is controlled by the size of the cell being detected plus its attached fluorescent label. The membrane hole size must be significantly less that the labeled cell because multiple holes in the membrane can concatenate into a larger hole that will allow the desired species to pass through. The total open area is also a factor in the concatenation effect, so the hole size and the hole count (open area) are chosen together such that the combination has a vanishingly small probability of the desired cells passing through. On the other hand, if the hole size is too small then cell particulates and unattached fluorophore will not pass through the membrane, which causes clogging and background fluorescence. Different tests will have different constraints on these 2 bounds, and will require different membrane hole sizes and open areas.

In the illustrated embodiment, the membranes 34 are held in place by tension; in other embodiments, the membranes 34 may be held in place by membrane holders with leak-tight gaskets. The collection membranes 34 may be clear or have black coatings to improve their use with fluorescent-based imaging systems. In this embodiment, one membrane 34 is used. The collection membrane 34 is generally hydrophobic (although the membranes 34 may also be hydrophilic), allowing the sample to remain in the collection chamber 14 until pressure is applied.

The absorbent pad 38 in this embodiment is rigid and provide the collection membrane(s) 34 a uniform, optically-flat surface (generally flat to within 10 $\mu$m, depending on optical system focal depth) on which to rest, thus keeping the entire surface of the membrane 34 within the depth of focus of the imaging system used to analyze the cellular elements trapped on the membrane 34. The pad 38 must also hold 1 to 2 mL or more of liquid and not change shape as the liquid is absorbed, since this could alter the flat surface upon which the membrane rests. In this embodiment, the pad 38 consists of a cylinder of sintered porous plastic; made of a high density polyethylene polymer with controlled pore sizes (in this embodiment, the pores are 45 to $90\mu$). In other embodiments, the pad 38 may be of other absorbent fibers. The pad 38 may be black or white depending on the wavelength of light being used in the fluorescent imaging system used to analyze the elements trapped on the membrane 34. The uniform sheets of sintered porons plastic are available from suppliers including Porex Technologies, Interflo Technologies, and MA Industries.

The pad 38 may be hydrophilic or hydrophobic. If the pad 38 is hydrophilic, fluid will be drawn by capillary action through the collection membrane 34 even in the absence of vacuum pressure. If the pad 38 is hydrophobic, the sample will remain on the surface of the collection membrane 34 until a small vacuum is added to draw the sample liquid through the membrane 34. One advantage of having a hydrophobic pad 38 is that a sample may be placed in the collection chamber 14 along with stain reagent and be incubated until vacuum pressure is applied.

The pad 38 volume is chosen to allow multiple additions of a sample into the top chamber and subsequently have the sample liquid retained in the volume of pad 38. Where concentrations of cells are very low (for instance, less than 0.01 cells/µL), it may be necessary to add multiple volumes of sample to obtain an accurate cell count.

A low-pressure vacuum, either a pumping system or a syringe, is applied at the vacuum port 18.

A cross-section of the assembled filter 10 is shown in FIG. 8. The collection membrane 34, the absorbent pad 38, all fit in the second chamber 26 of the device 10. Pad 38 is sufficiently rigid to retain membrane 34 fixed in position even when suction is applied. Membrane 34 and pad 38 are in contact over a sufficient surface to provide even support for membrane 34. This prevents membrane 34 from either slipping, sagging, or extruding from opening 16. As noted above in FIG. 1, the opening 16 at the bottom of the cylinder 14 matches the field of view of the imaging system used to analyze the cellular elements trapped on the collection membrane 34. Typical view fields for imaging systems are 3.0 mm diameter for 5× objective lens microscope systems, 1.7 mm for 10× objective systems, etc.

The height of the cylinder 14 is deep enough to hold the sample being concentrated (usually 100 to 300 µL) but shallow enough to allow for proper depth of focus by the imaging system. The diameter of the top opening of the cylinder 14 is large enough to allow for the introduction of the objective lens found in most imaging systems. The height of the entire device assembly 10 allows it to be placed under the objective arm of a fluorescent laboratory microscope. The width of the device assembly 10 is selected to allow it to fit onto the stage of a standard fluorescent laboratory microscope.

With respect to FIG. 9, the device 10 is shown on standard microscope 44 stage 46. A vacuum system 42 is attached to the device 10.

In another embodiment, the device can have multiple collection chambers. As shown in FIG. 10, the device may be part of a multiple-welled (i.e., 96, 384, 1536 wells, etc.) system or microplate 48 (the microplate 48 cross-section shown here shows 4 filters disposed in microplate wells.) Each well would have the same components of the "stand-alone" device 10 discussed above. The microplate 48 has a vacuum port 18 similar to the single device. A reader designed to image a microplate could analyze the results.

A number of different embodiments to the present illustrations are possible. The device may be molded or formed from a number of available materials. The top and bottom piece may attach by screwing or snapping together the pieces. Fluid may be drawn through the filter by pressure or pumping from the top as well as suction from the bottom. If a syringe is used, a single threaded port or other fitting could attach the syringe to each internal chamber. The absorbent material may be a single pad or a stack of pads or any other fluid retaining means.

The following section describes applications for and experiments using the device. The results from these applications/experiments are also included. The applications/experiments noted here are intended to be exemplary and are not intended to indicate limitations on uses for the device. In each of the following applications/experiments, the field of view was 1.7 mm in diameter, the collection membrane was 10µ thick with 1.0µ pores, and the absorbent pad was made of high density polypropylene with 45 to 90µ pores.

1) Avidin-Biotin Binding Pairs

Non-fluorescent 6.7µ latex beads were coated with biotin using standard coating procedures. After suspension of the washed beads in deionized water, avidin coated fluorescent beads 0.8µ in diameter (spherotech) were incubated with gentle mixing for 10 minutes. The smaller avidin coated beads were obtained commercially and came pre-loaded with fluorescent purple excitation 580 nm emission 620 nm (spherotech).

At the end of the incubation, a 50 µL sample of the suspension was applied to the device and the liquid allowed to drain assisted by a small vacuum pull from a manually operated 5 mL plastic syringe. The device was then placed into a reader and the 6.7µ latex beads, which were fluorescently labeled due to the avidin biotin binding, were imaged and counted. The resulting image is shown in FIG. 11. The smaller unbound fluorescent 0.8µ latex beads passed through the collection membrane. Size and intensity software gates eliminate any unbound beads still remaining on the collection membrane surface.

2) Low Level White Cell Counts in Spinal Fluid

Low levels of white cells in spinal fluid (<10 cells/µL) were measured by mixing 50 µL of spinal fluid with 100 µL of a solution of propidium iodide in Tris Buffer pH 7.4. The propidium iodide (PI) staining solution was made up according to Dzik, W. H. et al. Vox Sang. 59:153–159 (1990) and contained:

| | |
|---|---|
| Pi | 5 mg |
| Triton X-100 | 1 mL |
| ribonuclease | 5 mg |
| sodium citrate | 100 mg | in 100 mL DI water. After an incubation at room temperature of 5 minutes, 50 µL of the mixture was added to the device, filtered as discussed above, and the cells counted. The resulting image is shown in FIG. 12.

Typical normal total white cell counts in spinal fluid range from 1 to 10 cells/µL. In the above assay, a sample with 1 cell/µL will provide on average 16.6 cells in the field of view in the device for imaging and counting. Fractions of cells can not be counted therefore 16 or 17 cells per field of view will be recorded which is well within the required precision for this application. Because all final results are presented in whole numbers of cells only. Example, 0, 1, 2, 3, etc. cells/nL.

3) Granulocytes in Whole Blood

A solution of CD15 mouse monoclonal antibody labeled with biotin and diluted with phosphate buffered saline (50 µL) was mixed with 10 µL of whole blood and incubated for 10 minutes with mixing at room temperature. At the end of the incubation, 50 µL of a suspension of avidin-labeled fluorescent purple latex beads 0.8µ diameter (spherotech) was added. After 10 minutes incubation with mixing at room temperature, 50 µL of the suspension was added to the device, filtered as above, then read in the standard reader. The resulting image is shown in FIG. 13.

The specific measurement of the total number of granulocytes in clinical samples is used to monitor the response to various chemotherapeutic agents. White cell counts down to 100 cells/µL or less can be achieved in this assay format. For example, a sample with 100 cells/µL in the above assay will present 454.5 cells for imaging and counting.

4) Total Somatic Cells in Raw Whole Milk

A well mixed 50 µL sample of fresh whole raw milk was added to 300 µL of propidium iodide in Tris Buffer pH 7.4 with 0.05% Triton X-100 (octylphenoxypolyethoxy ethanol) a widely used non-ionic surfactant and incubated with mixing for 10 minutes at room temperature. A 50 µL sample of the mixture was then added to the device, filtered, and imaged as above. The resulting image is shown in FIG. 14.

Current practice in the dairy industry requires that whole raw milk intended for human consumption contain 500,000 total somatic cells or less/mL, or below 500 cells/µL. At 10,000 somatic cells/mL or 10/µL, the above assay procedure will result in 83 cells being counted in the device. This is well within the detection limit of the present invention and yet is 50 times below what is required in dairy laboratory practice.

5) Low Level White Cells in Transfusion Products

A well-mixed 100 µL sample of whole apheresis platelets was mixed with 100 µL propidium idodide in phosphate buffered saline pH 7.4 with 0.05% Triton X-100 at room temperature for 5 minutes. At the end of the incubation 50 µL of the mixture was added to the device and the cells counted and imaged as above. The resulting image is shown in FIG. 15.

A transfusion product with 0.2 cells/µL and a typical total volume of 300 mL will contain a total of 60,000 total white cells. The current United States standard for acceptable products is 5,000,000 white cells per product, while the European standard is 1,000,000 total cells. The device measures white cells in transfusion products at a detection limit which is 83 times the current requirement.

What is claimed is:

1. An apparatus for concentrating and measuring cells in biological samples comprising:
    a) a first chamber for receiving a biological sample, said first chamber having a sample introduction opening at a top end of said first chamber and a membrane placement opening at a bottom end of said first chamber;
    b) a collection membrane located below the membrane placement opening of the first chamber, said collection membrane able to trap cellular elements of the biological sample, said collection membrane placed in an optically level position;
    c) a second chamber adjacent to the first chamber, said second chamber having the membrane placement opening at a top end of the second chamber and a vacuum port at a bottom end of the second chamber;
    d) an absorbent pad located within the second chamber adjacent to the vacuum port and said collection membrane, said absorbent pad able to trap liquid from the biological sample; and
    e) a housing containing the apparatus, wherein the apparatus is configured to be placed on an imaging system stage for analysis.

2. The apparatus of claim 1 further wherein the membrane placement opening in the first chamber matches a field of view of an imaging system used to count cells.

3. The apparatus of claim 1 wherein the collection membrane is a polycarbonate track-etched membrane.

4. The apparatus of claim 1 wherein the first chamber has side walls treated to prevent cell adhesion and having a slope to enhance the flow of the biological sample.

5. The apparatus of claim 1 wherein the second chamber's vacuum port is configured so a syringe or pump may be attached to said vacuum port.

6. The apparatus of claim 1 wherein the collection membrane is hydrophobic.

7. The apparatus of claim 1 wherein the absorbent pad is hydrophilic.

8. The apparatus of claim 1 wherein the absorbent pad is hydrophobic.

9. An device for detecting cells comprising:
    a) a housing;
    b) a first chamber in said housing,
    c) a sample introduction opening at a top end of said first chamber;
    d) a membrane placement opening at a bottom end of said first chamber, said membrane placement opening having a smaller area than said sample introduction opening;
    e) a second chamber in said housing adjacent to said first chamber, said membrane placement opening at a top end of said second chamber;
    f) an outlet opening of said second chamber; and
    g) a membrane retained at an optically flat level below said membrane placement opening within said housing, said membrane having pores such that when a cell-containing liquid sample is introduced into said first chamber and a pressure differential created between said first and said second chamber, liquid flows through said membrane into said second chamber and cells are retained on said membrane, and wherein a membrane area defined by said membrane placement opening is matched to a size of an imaging system field of view.

10. The apparatus of claim 9 wherein the field of view provides a fixed area for cell counting.

11. The apparatus of claim 10 wherein the field of view provides a volumetric collection area which makes cell counting quantitative.

12. The apparatus of claim 9 further including an absorbent pad.

13. The apparatus of claim 12 wherein the absorbent pad is hydrophilic.

14. The apparatus of claim 12 wherein the absorbent pad is hydrophobic.

15. The apparatus of claim 9 wherein the at least one collection membrane is a polycarbonate track-etched membrane.

16. The apparatus of claim 9 wherein the first chamber has side walls having a slope to enhance the flow of the biological sample and said side walls are treated to prevent cell adhesion.

17. The apparatus of claim 9 wherein the second chamber's vacuum port is configured so a pump may be attached to said vacuum port.

18. The apparatus of claim 9 wherein at least one collection membrane is hydrophobic.

19. The apparatus of claim 9 wherein the apparatus is disposed in a well in a microplate.

20. A method of collecting and imaging cells, said method comprising:
    a) placing a sample liquid containing cellular elements in a chamber of an apparatus, the apparatus including said chamber and collection membrane;
    b) trapping cellular elements of the biological sample on collection membrane as liquid from the sample flows through the collection membrane;
    c) placing the apparatus on an imaging system stage; and
    d) viewing an entire cellular element collection area of said membrane in a single image by an imaging system.

21. The method of claim 20 further including labeling cellular elements of the sample in the chamber of the apparatus.

22. The method of claim 20 further including counting the cellular elements trapped on the collection membrane.

23. The method of claim 20 further including attaching a vacuum to the apparatus, said vacuum supplying pressure to draw liquid through the collection membrane.

24. The method of claim 20 further including a step following step a) and before step b) of incubating said sample in said chamber, wherein during said incubation targeted cellular elements are labeled with an optically detectable label.

25. The method of claim 20 further including using a hydrophobic collection membrane.

26. The method of claim 20 wherein the collection membrane provides a fixed area for cell counting.

27. The method of claim 26 wherein the collection membrane provides a volumetric collection area which makes cell counting quantitative.

28. The method of claim 20 further including performing steps a) through d) in a plate array having a plurality of chambers and collection membranes.

29. A multiwell plate for visualizing cells, the plate comprising a two-dimensional array of spaced cell-trapping devices, each device including:
   a) a first chamber for receiving a biological sample, said first chamber having a sample introduction opening at a top end of said first chamber and a membrane placement opening at a bottom end of said first chamber;
   b) a collection membrane located below the membrane placement opening of the first chamber, said collection membrane able to trap cellular elements of the biological sample, said collection membrane placed in an optically level position;
   c) a second chamber adjacent to the first chamber, said second chamber having the membrane placement opening at a top end of the second chamber and a vacuum port at a bottom end of the second chamber;
   d) a rigid and flat absorbent pad located within the second chamber adjacent to the vacuum port and said collection membrane, said absorbent pad able to trap liquid from the biological sample.

30. The plate of claim 29 wherein the membrane placement opening in the first chamber matches a field of view of an imaging system used to count cells.

31. The plate of claim 29 wherein the absorbent pad is hydrophilic.

32. The plate of claim 29 wherein the absorbent pad is hydrophobic.

33. The plate of claim 29 wherein said collection membrane is a polycarbonate track-etched membrane.

34. The plate of claim 29 wherein the first chamber has side walls having a slope and sail side walls are treated so that cells do not stick to enhance the flow of the biological sample.

35. The plate of claim 29 wherein collection membrane is hydrophobic.

36. The apparatus of claim 9 wherein said membrane retained at an optically flat level is flat to within 10 $\mu$m.

37. The apparatus of claim 9 wherein the pores on the membrane are smaller, than cell size.

38. The apparatus of claim 37 wherein the pores are smaller than 1 $\mu$m.

* * * * *